United States Patent [19]
Nakayama et al.

[11] Patent Number: 5,986,123
[45] Date of Patent: Nov. 16, 1999

[54] PREPARATION OF ALKYLHALOSILANES

[75] Inventors: Hiroshi Nakayama, Annaka; Tetsuo Nakanishi, Usui-gun; Kazumasa Tsukioka; Yukinori Satoh, both of Annaka, all of Japan

[73] Assignee: Shin-Etsu Chemical Co., Ltd., Tokyo, Japan

[21] Appl. No.: 09/053,059

[22] Filed: Apr. 1, 1998

[30]  Foreign Application Priority Data

Apr. 1, 1997  [JP]  Japan ................................. 9-098156

[51] Int. Cl.$^6$ ....................................... C07F 7/16

[52] U.S. Cl. ............................................. 556/472

[58] Field of Search ............................... 556/472

[56]  References Cited

U.S. PATENT DOCUMENTS

| | | | |
|---|---|---|---|
| 5,250,716 | 10/1993 | Mui | 556/472 |
| 5,312,948 | 5/1994 | Freeburne et al. | 556/472 |
| 5,380,903 | 1/1995 | Degen et al. | 556/472 |
| 5,618,960 | 4/1997 | Schulze et al. | 556/470 |

*Primary Examiner*—Paul F. Shaver
*Attorney, Agent, or Firm*—Millen, White, Zelano & Branigan, P.C.

[57]  ABSTRACT

An alkylhalosilane is prepared by charging a reactor with a contact mass comprising a metallic silicon powder and a copper catalyst, and feeding an alkyl halide into the reactor whereby the silane is formed by direct synthesis. The use of a metallic silicon powder having a specific particle size distribution ensures effective fluidization whereby the alkylhalosilane of quality is formed at a high selectivity and in high yields.

15 Claims, 1 Drawing Sheet

PREPARATION OF ALKYLHALOSILANES

BACKGROUND OF THE INVENTION

1. Field of the Invention

This invention relates to a method for preparing an alkylhalosilane by direct synthesis using metallic silicon powder and alkyl halide, and more particularly to a method for preparing an alkylhalosilane of quality at a high formation rate and a high selectivity and in high yields.

2. Prior Art

With respect to the synthesis of alkylhalosilanes, Rochow first disclosed in U.S. Pat. No. 2,380,995 direct synthesis reaction between metallic silicon and an alkyl halide in the presence of a copper catalyst. Since then, there have been reported a number of research works relating to various co-catalysts used together with copper catalysts, various copper catalysts and treatment thereof, reactors, additives used during reaction, and the like.

The direct synthesis process involves activating a mixture (often referred to as a contact mass) comprising metallic silicon, a copper catalyst and a co-catalyst, and introducing an alkyl halide into the activated contact medium for accomplishing gas-solid direct contact between metallic silicon and alkyl halide, thereby producing alkylhalosilanes. A fluidized bed reactor is generally used in industrial practice. If a uniform fluidized state is not established within the reactor, the formation rate of alkylhalosilanes will have a profile within the reactor and the rate of heat removal from within the system ceases to be uniform within the reactor. The loss of uniformity often causes the catalyst particles to be sintered and segregate from the contact mass and hot spots above the average temperature in the reactor to develop, giving rise to many problems including deactivation of the catalyst, decomposition of the alkyl halide and the alkylhalosilanes formed, impurity carbon build-up, a selectivity decline and a yield decline. Because of these problems, long-term continuous operation becomes difficult. Local deceleration of alkylhalosilane formation in the reactor undesirably results in a lowering of the overall formation rate of alkylhalosilanes.

For establishing a uniformly fluidized state, the particle diameter and particle size distribution of the contact mass powder are important factors. In general, a contact mass having a smaller mean particle diameter tends to invite a poorly fluidized state because particle agglomeration and a channeling phenomenon are likely to occur. For example, Kunii and Levenspiel, "Fluidization Engineering," Second Edition, 1991, describes that particles having a diameter of less than about 30 $\mu$m, divided into a particle group designated "Geldart C," are difficult to fluidize because of a strong force between particles.

It was believed that the metallic silicon powder in the reactor should preferably have a mean particle diameter of greater than 30 $\mu$m in order to establish a relatively good fluidized state. JP-A 202892/1990 corresponding to U.S. Pat. No. 5,015,751 discloses that the metallic silicon powder used in the synthesis of alkylhalosilanes should preferably have a mean particle diameter of up to 1,000 $\mu$m, especially up to 500 $\mu$m and that best results are obtained when the metallic silicon powder used has a mean particle diameter of 100 to 150 $\mu$m and a particle size distribution of 30 to 300 $\mu$m. Also, JP-B 5396/1991 corresponding to (U.S. Pat. No. 4,554,370) discloses that the silicon used in the fluidized bed should preferably have a particle size of up to 700 $\mu$m, a mean particle size of 20 to 300 $\mu$m, and a mean diameter in the range of 100 to 150 $\mu$m.

However, from the reaction point of view, as opposed to the establishing of a well fluidized state, it is usually preferred that the metallic silicon powder have a smaller particle diameter. The reason is that a smaller particle diameter ensures rapid and uniform reaction on account of the effective heat transfer between particles and the greater surface area of particles participating in the reaction. From this point of view, JP-A 188258/1995 corresponding to U.S. Pat. No. 5,312,948 discloses that the metallic silicon powder used in the direct synthesis reaction should preferably have a particle diameter in the range of 1 to 85 $\mu$m. Allegedly, strictly maintaining the metallic silicon powder within the above particle diameter range improves the selectivity of dialkyldihalosilane and the yield thereof from the starting reactant without detracting from fluidity. However, since particles having a diameter of less than 1 $\mu$m falling outside that range have a very large reactive surface area, the exclusion of these particles significantly reduces the reactive surface area, resulting in a drop of reactivity.

Therefore, it is an industrially important task to those skilled in the art that a metallic silicon powder satisfying both reactivity and fluidity can be utilized in the preparation of alkylhalosilanes.

SUMMARY OF THE INVENTION

An object of the invention is to provide a method for preparing an alkylhalosilane, typically a dialkyldihalosilane by a direct process, wherein the alkylhalosilane of quality is formed at a high formation rate and a high selectivity and in high yields using metallic silicon powder which has been regulated for appropriate fluidity.

The invention pertains to an industrially advantageous method for preparing an alkylhalosilane by direct synthesis, and especially to a method for preparing an alkylhalosilane through rapid and uniform reaction entailing a high selectivity of dialkyldihalosilane. Specifically, the invention pertains to a method for preparing an alkylhalosilane of the general formula (1):

$$R_n SiX_{4-n} \tag{1}$$

wherein R is an alkyl group having 1 to 4 carbon atoms, X is a halogen atom, and letter n is an integer of 0 to 4, comprising the steps of charging a reactor, typically a fluidized bed reactor, with a contact mass comprising a metallic silicon powder and a copper catalyst, and feeding a reactant gas containing an alkyl halide into the reactor whereby the silane is formed by direct synthesis. The metallic silicon powder used herein should satisfy the following Rosin-Rammler equation (2):

$$r = 100 exp(-bD^n) \tag{2}$$

wherein r is a weight percentage of particles having a greater diameter than D, b and n are constants, and n has a value of from more than 1.0 to less than 3.0. The use of this metallic silicon powder ensures good fluidity and greatly contributes to an improved selectivity of the end alkylhalosilane. When the metallic silicon powder has a particle size in the range of from more than 0 $\mu$m to 50 $\mu$m, and those particles having a diameter of up to 30 $\mu$m account for 90% of the volume base cumulative distribution, the reaction is accelerated to increase the rate of formation while maintaining the high selectivity of the end alkylhalosilane.

In one embodiment, scattering particles from the reactor may be used as the contact mass. More stable operation is expectable when the contact mass is heated in an inert atmosphere at a temperature of up to 350° C. before the start of reaction whereby the fluidized state is further improved and/or when the contact mass is controlled during continuous operation so that n may have a value in the above-defined range.

BRIEF DESCRIPTION OF THE DRAWINGS

The only FIGURE, FIG. 1 schematically illustrates a system for carrying out the alkylhalosilane preparation method of the invention.

DETAILED DESCRIPTION OF THE INVENTION

Figure 1:
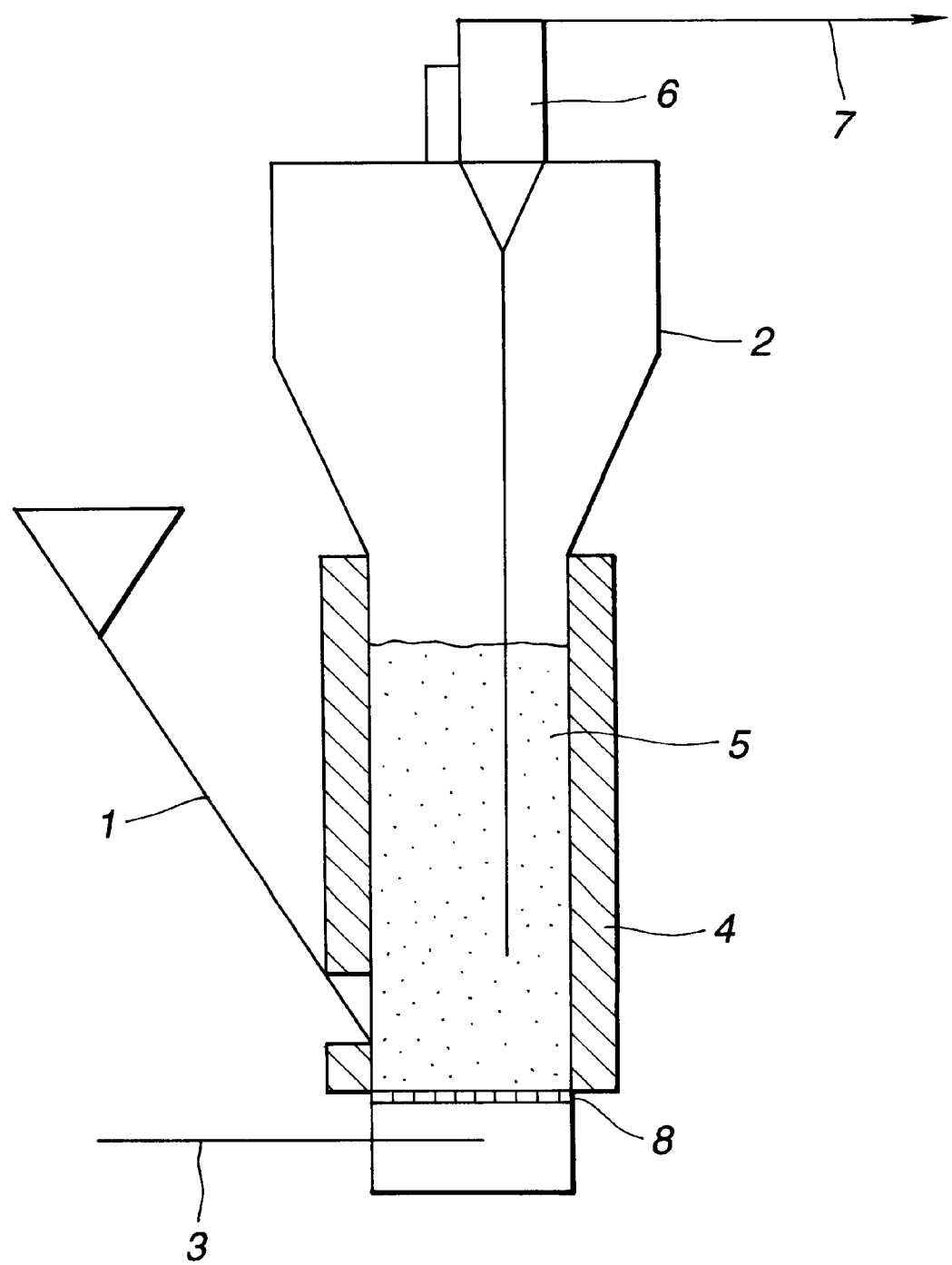

The alkylhalosilane preparing method according to the invention is to prepare an alkylhalosilane by direct synthesis from a metallic silicon powder, copper catalyst, co-catalyst, and alkyl halide. The reactor used herein may be any of well-known reactors such as fluidized bed reactors and agitating reactors. Fluidized bed reactors are preferred for industrial manufacture.

The metallic silicon powder used herein should preferably have a purity of at least 97% by weight, especially at least 98% by weight. The metallic silicon powder should have a particle size distribution represented by the following Rosin-Rammler equation (2):

$$r = 100 \exp(-bD^n) \tag{2}$$

wherein r is a weight percentage of particles having a greater diameter than D, b and n are constants, and n has a value of from more than 1.0 to less than 3.0, that is, $1.0 < n < 3.0$. The Rosin-Rammler equation is often used as an equation representing the particle diameter distribution of powder. It is well known to those skilled in the art that n in the equation is an index for rating the sharpness of particle diameter distribution. Investigating the relationship of the fluidity of metallic silicon powder to the value of n, we have found that controlling the value of n within the specific range ensures sufficient fluidity to produce the end alkylhalosilane at a high selectivity and in high yields. When the metallic silicon powder has a particle size in the range of from more than 0 $\mu$m to 50 $\mu$m, and those particles having a diameter of up to 30 $\mu$m account for 90% of the volume base cumulative distribution, the rate of formation of alkylhalosilane can be increased while maintaining the high selectivity.

Scattering particles from the reactor may be used as part or all of the metallic silicon powder. Better results are obtained when the contact mass or metallic silicon powder is heated for a certain time in an inert atmosphere at a temperature of up to 350° C., preferably 200 to 280° C. before it is subject to reaction. Preheating improves the fluidity and enables stable operation. When the contact mass is measured for particle diameter distribution at suitable intervals during continuous operation and an appropriate regulation is made such that n may have a value in the specific range, the operation becomes more stable.

The regulation of the mean particle diameter of the contact mass can be made mainly by regulating that of the metallic silicon powder as the raw material. For the regulation in mean particle diameter of the metallic silicon powder, various pulverizers such as roller mills, sand mills and ball mills may be used.

From the milled metallic silicon, a fraction of the desired particle size may be collected as by air elutriation. Since the metallic silicon powder collected by air elutriation has a very sharp particle size distribution, extra steps of separation and particle size regulation are unnecessary, which is advantageous for industrial manufacture. It is noted that the "particle size" is given by a volume base particle size distribution as measured by the laser diffraction/scattering process.

The method of the invention uses a copper catalyst. For the copper catalyst, any form of copper may be used, for example, elemental copper such as granular copper powder and stamped copper, copper alloys such as Cu-Zn, Cu-Si and Cu-Sb, and copper compounds such as cuprous oxide, cupric oxide, and copper halides. The copper catalyst is loaded in the reactor along with metallic silicon powder. The loading of the copper catalyst is preferably about 0.1 to 10 parts, especially about 2 to 8 parts by weight of copper per 100 parts by weight of the metallic silicon powder.

Together with the copper catalyst, an accelerator such as zinc, antimony, tin or arsenic may be used according to a well-known technique. An appropriate amount of the accelerator blended is 0.05 to 1 part by weight of zinc and 0.001 to 0.01 part by weight of antimony, tin, arsenic or a mixture thereof, per 100 parts by weight of the metallic silicon powder.

Alkyl halides are reacted with metallic silicon to form alkylhalosilanes. The alkyl halides used herein include methyl chloride, ethyl chloride, methyl bromide, and ethyl bromide. Among these, methyl chloride is commercially most useful. Dimethyldichlorosilane prepared using methyl chloride finds numerous applications as a raw material for a variety of silicone resins.

Desirably the alkyl halide reactant is previously heated and gasified before it is fed into the reactor. The alkyl halide gas may be used alone or in admixture with an inert gas. Examples of the inert gas include nitrogen gas, helium gas, and argon gas, with the nitrogen gas being cost effective. The feed amount of the alkyl halide gas is above the theoretical amount necessary to form an alkylhalosilane, and the flow rate of the alkyl halide gas combined with the inert gas is above the flow rate necessary to fluidize the contact mass.

The reaction temperature may be controlled in the range of 250 to 350° C. as is conventional, preferably in the range of 280 to 300° C. The reaction pressure may be controlled in the range of 0 to 10 atm. as is conventional, preferably in the range of 1 to 5 atm.

There has been described a method for preparing an alkylhalosilane, typically a dialkyldihalosilane by direct synthesis, wherein the alkylhalosilane of quality is formed through rapid uniform reaction at a high selectivity and in high yields, that is, in an industrially advantageous manner, while maintaining the contact mass in a fully fluidized state.

EXAMPLE

Examples of the invention are given below by way of illustration and not by way of limitation. In the following Examples, all percents and parts are by weight.

It is noted that the alkylhalosilane product contains dialkyldihalosilane (D), alkyltrihalosilane (T), and high-boiling products (R) having a boiling point above 80° C. The amounts of these components are expressed by percents by weight based on the total weight of the alkylhalosilane product. The formation rate of alkylhalosilane is represented by a space time yield (STY) which is equal to the weight of alkylhalosilanes produced per unit time relative to the weight of metallic silicon held in the reactor, that is, {weight (g) of alkylhalosilanes}/{weight (kg) of metallic silicon}× (time (hr.)}.

In the Examples, a reaction system having a fluidized bed reactor as shown in FIG. 1 was used for the preparation of alkylhalosilanes. The system shown in FIG. 1 includes a fluidized bed reactor 2 loaded with a contact mass 5 on a dispersing plate 8, a contact medium supply conduit 1 connected to the reactor 2, a gas supply conduit 3 connected to the reactor bottom, a heating jacket 4 surrounding the reactor 2, a cyclone 6 at the top of the reactor 2, and a conduit 7 for transporting the product gas from the reactor 2. Alkylhalosilanes are prepared in this system by feeding the contact mass 5 to the reactor 2 from the conduit 1, and introducing an inert gas therein from the gas supply conduit 3 to fluidize the contact mass. Then the reactor 2 is heated by means of the heating jacket 4 whereby the contact mass 5 is heated to the predetermined temperature, at which the contact mass 5 is kept fluidized for a certain time for activating the contact mass. Thereafter, the alkyl halide is introduced into the fluidized bed reactor 2 from the gas supply conduit 3 whereupon the alkyl halide is subject to gas-solid contact reaction with the contact mass to form alkylhalosilanes. The product gas is subject to gas-solid separation in the cyclone 6 and only the gas is delivered through the transport conduit 7.

Example 1

Nitrogen gas was passed through a fluidized bed reactor of carbon steel having a diameter of 80 mm and a height of 1,150 mm as shown in FIG. 1, and the reactor was heated to an internal temperature of 280° C. The reactor was then charged with a contact mass which had scattered during direct synthesis reaction and been recovered by a cyclone (n=2.7 in the Rosin-Rammler equation, mean particle diameter 7.5 $\mu$m, particle size range 0.1 to 40 $\mu$m, cumulative 90% diameter 14.7 $\mu$m). After the reactor interior temperature became stable, a gas mixture of 80% methyl chloride and nitrogen gas was introduced into the reactor which was maintained at a reaction temperature of 290° C. After the start of reaction, reaction was continued for 5 hours at a feed gas superfacial linear velocity of 0.07 m/sec. and a reactor interior pressure of 1.5 kg/cm$^2$.

Over the reaction time of 5 hours, the total formation rate of alkylhalosilanes was 356.1 g/kg-hr. The cumulative composition of the product was 90.8% of dimethyldichlorosilane, 3.5% of methyltrichlorosilane, and 2.5% of high-boiling products based on the methylchlorosilanes produced.

Example 2

Nitrogen gas was passed through a reactor as used in Example 1, and the reactor was heated to an internal temperature of 280° C. The reactor was then charged with a contact mass which had been withdrawn from a reactor of direct synthesis reaction (n=1.6 in the Rosin-Rammler equation, mean particle diameter 60.3 $\mu$m, particle size range 0.1 to 150 $\mu$m, cumulative 90% diameter 120.5 $\mu$m). After the reactor interior temperature became stable, a gas mixture of 80% methyl chloride and nitrogen gas was introduced into the reactor which was maintained at a reaction temperature of 290° C. After the start of reaction, reaction was continued for 5 hours at a feed gas superfacial linear velocity of 0.07 m/sec. and a reactor interior pressure of 1.5 kg/cm$^2$.

Over the reaction time of 5 hours, the total formation rate of alkylhalosilanes was 206.8 g/kg-hr. The cumulative composition of the product was 88.4% of dimethyldichlorosilane, 4.2% of methyltrichlorosilane, and 2.3% of high-boiling products based on the methylchlorosilanes produced.

Example 3

Nitrogen gas was passed through a reactor as used in Example 1, and the reactor was heated to an internal temperature of 280° C. The reactor was then charged with 100 parts of industrial grade metallic silicon powder (n=1.8 in the Rosin-Rammler equation, mean particle diameter 58.1 $\mu$m, particle size range 0.1 to 150 $\mu$m, cumulative 90% diameter 122.3 $\mu$m) and 2.7 parts of a catalyst mixture containing copper chloride powder as the major component. While the reactor interior temperature was maintained at 280° C., nitrogen gas was passed for 2 hours for fluidization. A gas mixture of 80% methyl chloride and nitrogen gas was then introduced into the reactor which was maintained at a reaction temperature of 290° C. After the start of reaction, reaction was continued for 5 hours at a feed gas superfacial linear velocity of 0.07 m/sec. and a reactor interior pressure of 1.5 kg/cm$^2$.

Over the reaction time of 5 hours, the total formation rate of alkylhalosilanes was 189.5 g/kg-hr. The cumulative composition of the product was 87.8% of dimethyldichlorosilane, 6.0% of methyltrichlorosilane, and 2.3% of high-boiling products based on the methylchlorosilanes produced.

Example 4

Nitrogen gas was passed through a reactor as used in Example 1, and the reactor was heated to an internal temperature of 280° C. The reactor was then charged with 100 parts of industrial grade metallic silicon powder (n=1.8 in the Rosin-Rammler equation, mean particle diameter 54.7 $\mu$m, particle size range 0.1 to 186 $\mu$m, cumulative 90% diameter 115.3 $\mu$m) and 2.7 parts of a catalyst mixture containing copper chloride powder as the major component. Thereafter, a gas mixture of 80% methyl chloride and nitrogen gas was introduced into the reactor which was maintained at a reaction temperature of 290° C. After the start of reaction, reaction was continued for 5 hours at a feed gas superfacial linear velocity of 0.07 m/sec. and a reactor interior pressure of 1.5 kg/cm$^2$.

Over the reaction time of 5 hours, the total formation rate of alkylhalosilanes was 172.2 g/kg-hr. The cumulative composition of the product was 87.0% of dimethyldichlorosilane, 6.2% of methyltrichlorosilane, and 2.5% of high-boiling products based on the methylchlorosilanes produced.

Example 5

Nitrogen gas was passed through a reactor as used in Example 1, and the reactor was heated to an internal temperature of 280° C. The reactor was then charged with a contact mass which had been withdrawn from a reactor of direct synthesis reaction (n=1.0 in the Rosin-Rammler equation, mean particle diameter 55.1 $\mu$m, particle size range 0.1 to 200 $\mu$m, cumulative 90% diameter 150.5 $\mu$m). After the reactor interior temperature became stable, a gas mixture of 80% methyl chloride and nitrogen gas was introduced into the reactor which was maintained at a reaction temperature of 290° C. After the start of reaction, reaction was continued for 5 hours at a feed gas superfacial linear velocity of 0.07 m/sec. and a reactor interior pressure of 1.5 kg/cm$^2$.

Over the reaction time of 5 hours, the total formation rate of alkylhalosilanes was 198.3 g/kg-hr. The cumulative composition of the product was 86.5% of dimethyldichlorosilane, 6.2% of methyltrichlorosilane, and 2.9% of high-boiling products based on the methylchlorosilanes produced.

Comparative Example 1

Nitrogen gas was passed through a reactor as used in Example 1, and the reactor was heated to an internal temperature of 280° C. The reactor was then charged with a contact mass which had scattered during direct synthesis reaction and been recovered by a cyclone (n=0.9 in the Rosin-Rammler equation, mean particle diameter 11.3 μm, particle size range 0.1 to 69 μm, cumulative 90% diameter 27.5 μm). After the reactor interior temperature became stable, a gas mixture of 80% methyl chloride and nitrogen gas was introduced into the reactor which was maintained at a reaction temperature of 290° C. After the start of reaction, reaction was continued for 5 hours at a feed gas superfacial linear velocity of 0.07 m/sec. and a reactor interior pressure of 1.5 kg/cm².

Over the reaction time of 5 hours, the total formation rate of alkylhalosilanes was 273.1 g/kg-hr. The cumulative composition of the product was 85.8% of dimethyldichlorosilane, 7.7% of methyltrichlorosilane, and 3.6% of high-boiling products based on the methylchlorosilanes produced.

Comparative Example 2

Nitrogen gas was passed through a reactor as used in Example 1, and the reactor was heated to an internal temperature of 280° C. The reactor was then charged with 100 parts of industrial grade metallic silicon powder (n=0.8 in the Rosin-Rammler equation, mean particle diameter 52.8 μm, particle size range 0.1 to 186 μm, cumulative 90% diameter 140.1 μm) and 2.7 parts of a catalyst mixture containing copper chloride powder as the major component. Then a gas mixture of 80% methyl chloride and nitrogen gas was introduced into the reactor which was maintained at a reaction temperature of 290° C. After the start of reaction, reaction was continued for 5 hours at a feed gas superfacial linear velocity of 0.07 m/sec. and a reactor interior pressure of 1.5 kg/cm².

Over the reaction time of 5 hours, the total formation rate of alkylhalosilanes was 145.8 g/kg-hr. The cumulative composition of the product was 84.8% of dimethyldichlorosilane, 8.2% of methyltrichlorosilane, and 4.1% of high-boiling products based on the methylchlorosilanes produced.

The results of the foregoing Examples and Comparative Examples are shown in Table 1.

as to be 1.0<n<3.0 and the particle size range is controlled within the preferred range of the invention.

Although some preferred embodiments have been described, many modifications and variations may be made thereto in the light of the above teachings. It is therefore to be understood that within the scope of the appended claims, the invention may be practiced otherwise than as specifically described.

We claim:

1. A method for preparing an alkylhalosilane of the general formula (1):

$$R_nSiX_{4-n} \quad (1)$$

wherein R is an alkyl group having 1 to 4 carbon atoms, X is a halogen atom, and letter n is an integer of 0 to 4, comprising the steps of charging a reactor with a contact means comprising a metallic silicon powder and a copper catalyst, and feeding a reactant gas containing an alkyl halide into the reactor whereby the silane is formed by direct synthesis, the metallic silicon powder satisfying the following Rosin-Rammler equation (2):

$$r=100exp(-bD^n) \quad (2)$$

wherein r is a weight percentage of particles having a greater diameter than D, b and n are constants, and n has a value of from more than 1.0 to less than 3.0.

2. The method of claim 1 wherein the metallic silicon powder has a particle size in the range of from more than 0 μm to 50 μm, and those particles having a diameter of up to 30 μm account for 90% of the volume base cumulative distribution.

3. The method of claim 1 wherein part or all of the contact mass comprises scattering particles from the reactor.

4. The method of claim 1 further comprising the step of heating the contact mass in an inert atmosphere at a temperature of up to 350° C. before the start of reaction.

5. The method of claim 1 wherein during continuous operation, the contact mass is maintained so that n has a value of from more than 1.0 to less than 3.0.

TABLE 1

|  | E1 | E2 | E3 | E4 | E5 | CE1 | CE2 |
|---|---|---|---|---|---|---|---|
| n value | 2.7 | 1.6 | 1.8 | 1.8 | 1 | 0.9 | 0.8 |
| Mean particle diameter (μm) | 7.5 | 60.3 | 58.1 | 54.7 | 55.1 | 11.3 | 52.8 |
| Particle size range (μm) | 0.1–40 | 0.1–150 | 0.1–150 | 0.1–186 | 0.1–200 | 0.1–69 | 0.1–186 |
| Cumulative 90% diameter (μm) | 14.7 | 120.5 | 122.3 | 115.3 | 150.5 | 27.5 | 140.1 |
| Cumulative D (wt %) | 90.8 | 88.4 | 87.8 | 87 | 86.5 | 85.8 | 84.8 |
| Cumulative T (wt %) | 3.5 | 4.2 | 6 | 6.2 | 6.2 | 7.7 | 8.2 |
| Cumulative R (wt %) | 2.5 | 2.3 | 2.3 | 2.5 | 2.9 | 3.6 | 4.1 |
| Cumulative STY (g/kg-hr) | 356.1 | 206.8 | 189.5 | 172.2 | 198.3 | 273.1 | 145.8 |

It is evident from Table 1 that the selectivity of dialkyldihalosilane is improved when the value of n is controlled within the range of the invention. Example 1 using the scattering contact mass from the reactor shows that the selectivity and formation rate of dialkyldihalosilane are significantly improved when the value of n is controlled so 6. The method of claim 1, wherein the alkylhalosilane is a dialkyldihalosilane.

7. The method of claim 1, wherein the metallic silicon powder has a purity of at least 97% by weight.

8. The method of claim 1, wherein the copper catalyst is elemental copper, a copper alloy or a copper compound.

9. The method of claim 1, wherein the copper catalyst is granular copper powder stamped copper, Cu-Zn alloy, Cu-Si alloy, Cu-Sb alloy, a copper oxide or a copper halide.

10. The method of claim 1, wherein the loading of the copper catalyst is about 0.1 to 10 parts by weight of copper per 100 parts by weight of the metallic silicon powder.

11. The method of claim 1, wherein a zinc, antimony, tin or arsenic accelerator is used together with the copper catalyst.

12. The method of claim 1, wherein the alkyl halide is methyl chloride, ethyl chloride, methyl bromide or ethyl bromide.

13. The method of claim 1, wherein the alkyl halide is methyl chloride and the alkylhalosilane produced is dimethyldichlorosilane.

14. The method of claim 1, wherein the reaction temperature is 250 to 350° C. and the reaction pressure is 0 to 10 atm.

15. The method of claim 1, wherein the reaction temperature is 280 to 300° C. and the reaction pressure is 1 to 5 atm.

* * * * *